| United States Patent [19] | [11] Patent Number: 4,769,038 |
| Bendavid et al. | [45] Date of Patent: Sep. 6, 1988 |

[54] PROSTHESES AND TECHNIQUES AND REPAIR OF INGUINAL AND FEMORAL HERNIAS

[75] Inventors: Robert Bendavid, Thornhill, Canada; Milo A. Titone, Wilmington, Del.

[73] Assignee: C. R. Bard, Inc., Murray Hill, N.J.

[21] Appl. No.: 840,783

[22] Filed: Mar. 18, 1986

[51] Int. Cl.[4] .......................... A61F 2/08; A61B 17/04
[52] U.S. Cl. ........................................ 623/13; 623/11; 128/334 R; 66/193
[58] Field of Search ............... 128/334 R, 334 C, 155, 128/156; 623/13, 14, 11; 66/193, 192, 169 R, 202, 195

[56] References Cited

U.S. PATENT DOCUMENTS

| 1,054,233 | 2/1913 | Mueller | 66/195 |
| 3,625,209 | 12/1971 | Clark | 128/156 X |
| 3,965,703 | 6/1976 | Barnhardt | 66/193 |
| 3,986,828 | 10/1976 | Hoffman, Jr. et al. | 66/169 R |
| 4,176,664 | 12/1979 | Kalish | 128/156 |
| 4,452,245 | 6/1984 | Usher | 128/334 R |

FOREIGN PATENT DOCUMENTS

497411 11/1953 Canada ................. 128/156

*Primary Examiner*—Richard J. Apley
*Assistant Examiner*—Alan W. Cannon
*Attorney, Agent, or Firm*—Wolf, Greenfield & Sacks

[57] ABSTRACT

Prosthesis for repair of inguinal hernias and femoral hernias are provided, together with techniques for implanting the prostheses. The inguinal prosthesis has three panels which radiate from a common elongate core. The core serves as a replacement for the inguinal ligament and the panels are attached to selected musculature and ligamentous tissue. One of the panels is sutured to Cooper's ligament, a second panel is sutured to the conjoined tendon and the third panel is sutured to the exterior oblique aponeurosis. A prosthesis for repair of femoral hernias also is provided and is in the form of an umbrella-shaped device having a top panel and a stem which is attached to the face and extends generally perpendicular from the top panel. The prosthesis may be implanted in a relatively simple procedure in which the femoral ring, through which the hernia has occurred is exposed surgically from below. The top panel of the prosthesis is folded downwardly about the stem in umbrella-like fashion and is urged upwardly through the femoral ring. Once the top panel is above the femoral ring, it can expand and rest securely on the region about the femoral ring. After the top panel has been so placed, the stem is severed and removed, leaving the top panel in place.

6 Claims, 7 Drawing Sheets

PATTERN CHAIN READINGS

| BAR 3 | BAR 5 | BAR 7 | BAR 10 | BAR 12 |
|---|---|---|---|---|
| 0 | 2 | 2 | 2 | 0 |
| 0 | 0 | 0 | 2 | 0 |
| 0 | 0 | 0 | 2 | 6 |
| 0 | 0 | 2 | 0 | 6 |
| 6 | 0 | 2 | 0 | 6 |
| 6 | 2 | 0 | 0 | 6 |
| 6 | 2 | 0 | 0 | 0 |
| 6 | 2 | 2 | 2 | 0 |

PROSTHESES AND TECHNIQUES AND REPAIR OF INGUINAL AND FEMORAL HERNIAS

FIELD OF THE INVENTION

This invention relates to surgical prostheses and techniques for use in the repair of inguinal and femoral hernias.

BACKGROUND OF THE INVENTION

A hernia is the formation of an opening in the abdominal wall typically accompanied with abdominal tissue and viscera which pushes through the opening in the abdominal wall. The abdominal wall has several relatively weak regions where hernias tend to occur with greatest frequency. These include the inguinal canal and the femoral ring.

The treatment of a hernia in a patient's abdominal wall frequently involves surgery in an effort to repair the defect. The abdominal tissue that has pushed through the defect in the abdominal wall includes a sack lined by the peritoneum with viscera contained in the sack. Treatment requires that the contents of the sack be returned to a normal position in the abdomen or, if that cannot be done, the protruding sack and viscera must be removed surgically. The defect in the abdominal wall then is surgically repaired by suturing the ruptured muscle in an effort to close the defect and restore the integrity of the abdominal wall.

Conventional procedures for hernia repair frequently provide only temporary relief. Typically, they involve stretching of the musculature and ligamentous tissue in order to close the defect. The tissues are sutured while in a stretched configuration which makes the abdominal wall further susceptible to a recurring hernia. Surgical correction of a recurring hernia typically results in further degeneration of the involved muscles and ligaments.

In an effort to avoid recurring hernias and the resulting progressive deterioration surgeons commonly use sheets of implantable mesh material, such as a knitted polypropylene fabric available under the designation Marlex mesh. The sheet of polypropylene mesh material is placed over the defect and may be sutured in place as determined by the surgeon. Although some hernias may be treated in that manner with some success, many ultimately result in failure and recurrence of the hernia.

After a number of surgical treatments for recurring inguinal hernias, a patient's inguinal ligament often deteriorates to a point of total or near total destruction. Often the results of such recurrent hernia is that the floor of the inguinal canal and iliopubic tract also are totally destroyed or severely deteriorated so that there is no site to which the abdominal muscles can be reattached. There has been no effective treatment for such patients and they often must wear an external appliance, or truss, to hold in the viscera and bowels.

It is among the objects of the present invention to provide a novel prosthetic device which facilitates surgical repair and reconstruction of an otherwise unrepairable inguinal hernia and by a technique which relieves the problem with very substantially reduced risk of reoccurrence.

Another commonly encountered type of hernia is the femoral hernia, which forms in the femoral ring in the iliopubic tract spanning the gap between the inguinal ligament and the pubic bone. Surgical repair of a femoral hernia typically has involved extensive surgery in which the patient is under general anesthesia. The femoral hernia normally is repaired by stretching the herniated, relatively thin lacunar ligament to close the defect. That procedure also tends to stretch and, therefore, weaken the involved region and enhances the chance of recurrence. It also is among the general objects of the invention to provide a new prosthesis and surgical technique for repair of femoral hernias which may be performed quickly and, in some cases, under local anesthesia while minimizing the chance of recurrence.

SUMMARY OF THE INVENTION

The prosthetic device for use in repair of inguinal hernias includes an arrangement of three panels of sheet material which are joined along and radiate from a common elongate core. The core serves as a prosthetic replacement for the inguinal ligament. When implanted, it is sutured at its ends to the remaining remnants of the inguinal ligament, at the aterior superior iliac spine and the pubic tubercle. The first of the three panels then is sutured to Cooper's ligament. The second panel is sutured to the conjoined tendon at the lower margin of the internal oblique muscle. The third panel is sutured to the external oblique aponeurosis. The arrangement of panels enables the herniated muscles of the abdominal wall to be reconstructed with the panels of the prosthesis in a manner which avoids stretching of the musculature which has been typical of the prior surgical techniques and which often resulted in recurrence of the hernia. The abdominal wall, as reconstructed with the three panel prosthetic, is very strong and greatly reduces the chance of recurrence of the hernia.

The prosthesis is formed from a sheet of material which is biologically compatible, flexible and porous to enable tissue ingrowth. The prosthesis material also is strong enough to assure that the anchoring sutures will not pull out. The panels of the prosthesis also may be trimmed to a desired shape without unraveling or fraying so as to be fitted to the particular contour of the patient's anatomy. In a preferred embodiment of the invention the prosthesis is formed from a fabric of knitted polypropylene monofilament yarn. Preferably the knitted prosthesis is knitted as a single integral unit on a double needle bed Raschel knitting machine in which a wide band of a two bar fabric is knitted on one bed and a narrow band of a two bar fabric is knitted on the other bed, with the edge of the narrower band being knitted to the face of the wider band. In the preferred embodiment each of the knitted fabric bands comprises laid in yarns trapped by a chain stitch with the bands being connected by a chain stitch. The juncture of the bands defines the strengthened core of the prosthesis with the two halves of the wide band and the single narrow band defining the three panels.

The prosthesis for treatment of the femoral hernia includes a sheet of prosthetic material, such as a fabric of the type used in connection with the inguinal prosthesis described above. The sheet is attached to a stem which extends generally perpendicular from the plane of the sheet in an umbrella-like fashion. The stem serves as a means by which the prosthetic sheet may be inserted and manipulated into position. The device is implanted by surgically exposing the femoral ring from below the inguinal canal and pushing the umbrella-like prosthesis, by its stem, upwardly through the femoral ring into the inguinal canal. The stem is used to manipulate the prosthetic sheet so that it lies within the inguinal canal and expands to cover the opening of the femoral ring adjacent the femoral sheath. It may be securely located by suturing it to Cooper's ligament, to the inguinal ligament and to the femoral sheath. Once the top piece of the umbrella prosthetic has been placed, the stem can be cut away and removed. The operation then may be concluded by suturing the incision. The prosthetic may be placed with the use of local anesthetic.

It is among the general objects of the invention to provide a new prosthesis for repair of inguinal hernias, particularly inguinal hernias which have recurred to an extent in which the inguinal ligament is completely deteriorated or has deteriorated to an extent in which it is no longer useful for surgical repair.

A further object of the invention is to provide an improved technique for repairing inguinal hernias.

Another object of the invention is to provide a new prosthesis for surgical repair of femoral hernias.

A further object of the invention is to provide an improved surgical technique for the repair of femoral hernias.

DESCRIPTION OF THE DRAWINGS

The foregoing and other objects and advantages of the invention will be appreciated more fully from the following further description thereof with reference to the accompanying drawings in which.

DESCRIPTION OF THE PREFERRED EMBODIMENT

Figure 1:
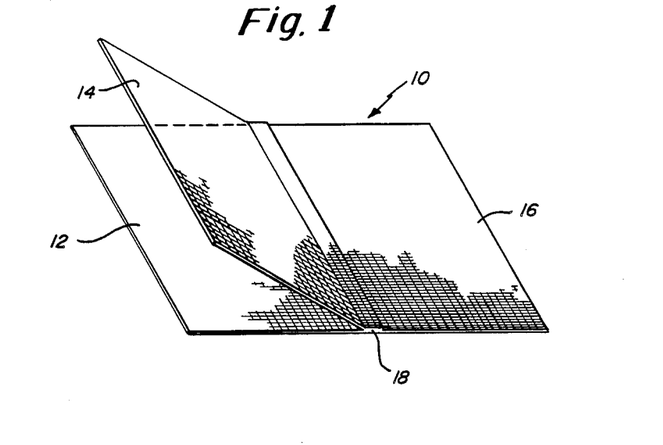
FIG. 1 is an illustration of the three panel inguinal prosthesis.

FIG. 1 illustrates a prosthesis in accordance with the invention for use in repair of inguinal hernias. The prosthesis is formed from a flexible sheet of biologically compatible material and preferably has a structure defined by interstices to enable tissue to grow into and incorporate the material. The prosthesis 10 is formed to define three panels including a first panel 12, second panel 14 and third panel 16. The panels 12, 14, 16 extend radially outwardly from a common elongate central junction or core 18. Although the preferred structure for the prosthesis 10 is a mesh knitted from polypropylene fiber, as will be further described, it should be understood that other sheet materials having the desired properties may be found suitable for use in the practice of the invention.

Figure 2:
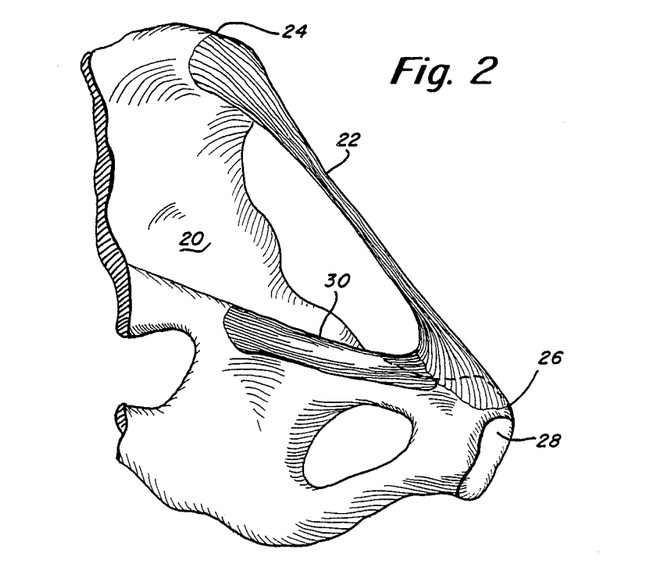
FIG. 2 is an illustration of the anatomy of the right anterior region of the pelvic bone to illustrate the location of the inguinal ligament and Cooper's ligament, the figure being a view from above and medially of the pelvic region and viewed in an oblique, lateral direction.

FIG. 2 illustrates the portion of the region of the pelvic bone, indicated generally at 20, which includes the inguinal region. The ends of the inguinal ligament 22 are attached to the pelvic bone at the anterior superior iliac spine 24 and the pubic tubercle 26. Although not fully illustrated in FIG. 2, the inguinal ligament 22 extends along the lower edge of the external oblique aponeurosis, which forms the lower extension of one of the abdominal muscles, the external oblique muscle. Also of importance in the placement of the prosthesis is the ligamentous tissue along that portion of the pubic bone 28 which is referred to as Cooper's ligament 30.

Figures 3, 4:
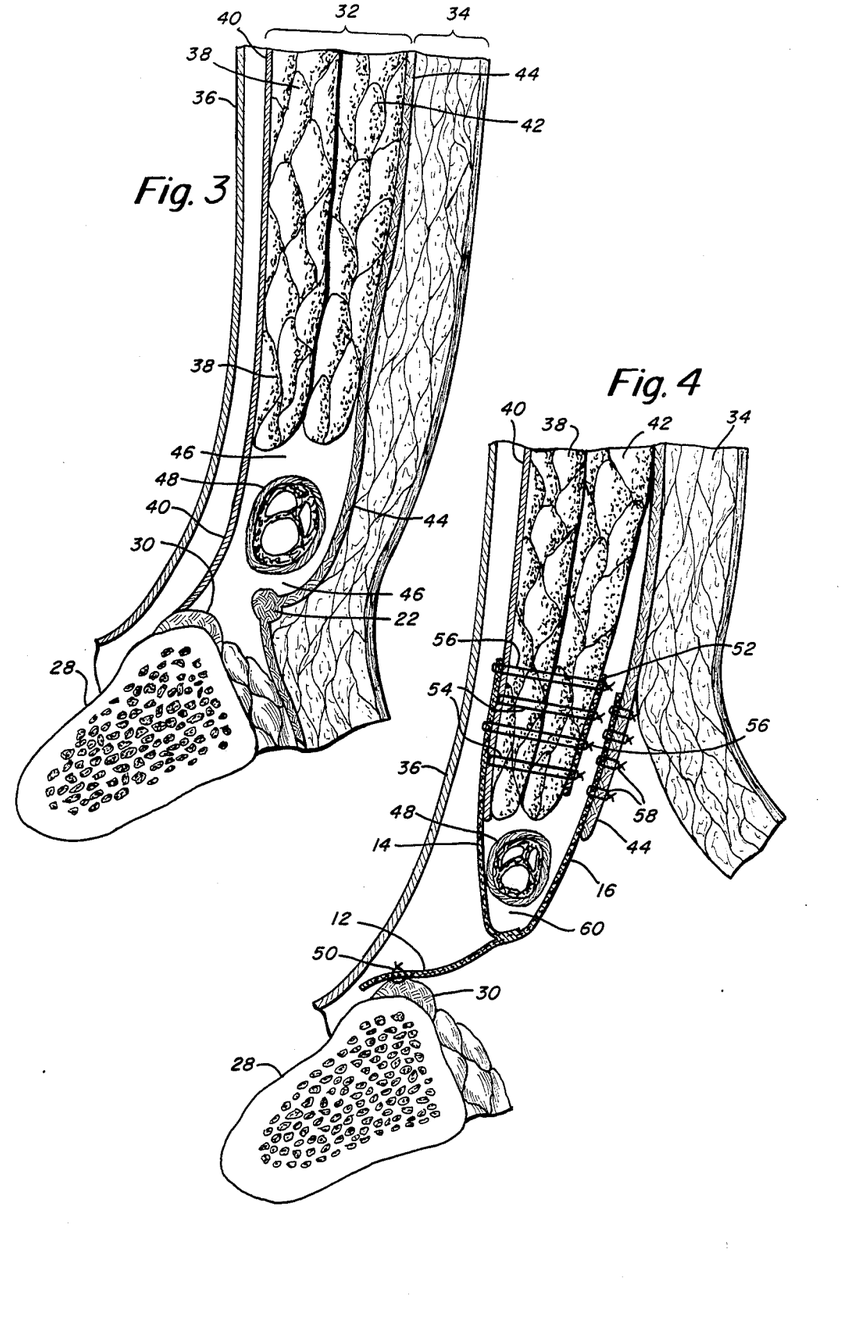
FIG. 3 is a sectional illustration as seen along a plane generally perpendicular to the direction of the inguinal ligament and intersecting the pubic bone in the region of Cooper's ligament, and illustrating, somewhat diagrammatically, the anatomy of the inguinal region.
FIG. 4 is a sectional illustration similar to FIG. 3 showing, diagrammatically, the placement of the prosthesis as seen along the line 4—4 of FIG. 5.

FIG. 3 illustrates, somewhat diagrammatically, further details of the anatomy of the inguinal region. FIG. 3 shows the region as seen along the axis of the inguinal ligament 22 and at a plane passing through the pubic bone 28 and Cooper's ligament 30. The abdominal wall, indicated generally at 32 lies between the layers of skin and subutaneous fat 34 and the peritoneum 36 which contains the intestines. A hernia is the result of a weakness or defect in one or more of the layers of the abdominal wall 32 through which the peritoneum and intestines may push, as when subjected to increased internal abdominal pressure.

The abdominal wall 32 in the inguinal region includes the transversus muscle 38 and transversalis fascia 40, the internal oblique muscle 42 and the external oblique aponeurosis 44. The external oblique aponeurosis 44 is a thin sheet of ligamentous tissue, which extends inferiorally of the external oblique muscle. The inguinal ligament 22 is formed integrally with and defines the lower edge of the external oblique aponeurosis 44. The region between the lower portion of the external oblique aponeurosis 44 and the lower region of the transversalis fascia 40 defines the inguinal canal 46 which contains a portion of the spermatic cord 48.

Many techniques have been used in the surgical repair of inguinal hernias. After the peritoneum 36 and intestine which it may contain is pushed back into the abdominal cavity or is surgically removed, the defect in the abdominal wall must be repaired. Many of surgical techniques for hernia repair involve stretching of abdominal muscles, aponeuroses and fascia and suturing them to close the defect. Many procedures involve anchoring of the musculature and ligamentous tissue to the inguinal ligament.

That places additional strain on the inguinal ligament which tends to further stretch and weaken it. Should the hernia recur, the surgical procedure typically will be repeated. With each successive surgical treatment for an inguinal hernia, it may be necessary for the surgeon to trim away from the muscles and ligamentous tissue scar the tissue from previous hernia operations. That shortens the muscle and requires stretching of the muscle to enable it to be attached. After a number of surgical treatments for an inguinal hernia, it is not uncommon for the inguinal ligament 22 to be so stretched and weakened, or completely destroyed as to be of no further use in corrective surgery. Patients having such a condition have had little hope of it being corrected.

In many cases, surgeons find it desirable to use patches of fabric to which may be placed over the sutured to the patient's muscles in an attempt to reinforce the abdominal wall or to cover a defect in the wall. Although the use of such patches has had varying success and, in some cases is quite successful, there has not yet been a prosthesis capable of repairing the entire inguinal region including prosthetic replacement of the inguinal ligament.

Figure 5:
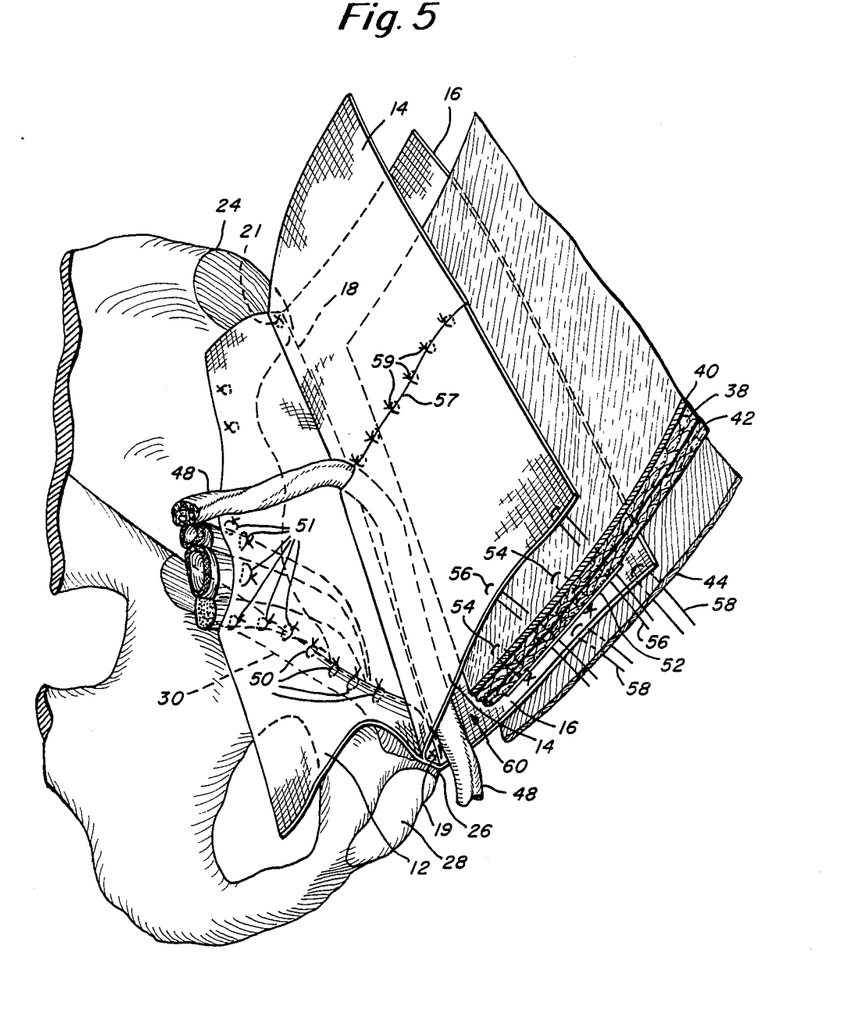
FIG. 5 is another illustration of the placement of the inguinal prosthesis.

In accordance with the present invention, the three panel prosthesis 10 is implanted, as illustrated in FIGS. 4 and 5, so that the central core 18 serves as a prosthetic replacement for the inguinal ligament 22. With the ends of the core 18 securely anchored, as by sutures 19, 21 the panels, 12, 14, 16 are sutured to muscle and ligamentous tissue in a manner which reconstructs effectively the herniated inguinal region and prevents recurrence of the hernia.

The prosthesis should be provided in a length greater than that which can be expected for the patient, that is, it should be longer than the distance between the patient's anterior superior iliac spine 24 and pubic tubercle 26. The prosthesis is trimmed to the desired length and the ends of the central core 18 are sutured to the remnants of the inguinal ligament 22, at the anterior superior iliac spine 24 and pubic tubercle 26, respectively. After the prosthesis has been anchored, one of the panels, e.g., the first panel 12, is sutured, as at 50, to Cooper's ligament 30. A number of sutures 50 should be placed to attach securely the margin of the first panel 12 to and along Cooper's ligament 30. Before suturing the first panel 12 to Cooper's ligament 30, the surgeon may trim and shape the first panel 12 so that it approximates the curve of Cooper's ligament. A number of sutures 51 also may be made to attach a portion of the first panel 12 to the femoral sheath.

After the first panel 12 has been sutured in place, a second panel, e.g., panel 14, is attached to the conjoined tendon at the lower end of the combined internal oblique muscle 42, transversus muscle 38 and transversalis fascia 40. In order to enhance the strength of the sutures and to reduce the chance of suture pull out, a strip 52 of material which may be the same as that from which the prosthesis 10 is made, is itself sutured, as at 54, to the aterior surface of the conjoined tendon. After the reinforcing strip 52 is attached, the second panel 14 is placed against the posterior side of the transversalis fascia and a number of sutures 56 are formed across the combined layers. Preferably the strip 52 and second panel 14 are placed to extend well inwardly from the margin of the conjoined tendon.

The second panel is cut as indicated at 57 to enable the spermatic cord to be passed through the panel. The spermatic cord passes through the cut panel in proximity to the core of the prosthesis, the portion to which the spermatic cord passes serving as the equivalent of the patient's internal ring. The cut second panel then may be resutured as indicated at 59.

The third panel, e.g., panel 16, then is attached by suturing it to the remainder of the margin of the external oblique aponeurosis 44 by sutures 58. The spermatic cord 48 is shown in FIGS. 4 and 5 as being disposed between the second and third panels 14, 16 in a prosthetically defined canal 60. The panels 12, 14 cooperate to define somewhat of a hammock-like structure which serves as a very strong region to contain the peritoneum 36 and in a manner which prevents recurrence of the hernia.

The panels 12, 14, 16 should be formed from a flexible, easily handled yet strong material and should be able to withstand pressures of the order of at least 50 psi (measured by the Mullen burst test) which is the approximte equivalent of a strong cough. The panels should be capable of being cut and trimmed without unraveling or separating. The panels also should be formed from a material and in a manner which is sufficiently porous and has ample openings for tissue ingrowth with maximum strength.

By way of illustrative example, the panels may be formed from a warp knitted fabric knitted from six mil polypropylene yarn, 150 denier. The prosthesis may be made in a two needle bar Raschel knitting machine such as a DE14 Fashion Master machine, although other two bar warp knitting machines may be used. The prosthesis may be knit by knitting a full width panel on one of the needle beds of the machine and by knitting a half width panel on the other needle bed of the machine. The edge of the half width fabric is connected to the midline of the full width fabric by chain stitches, stitching from one needle bed to the other needle bed. The three panel configuration thus may be knit continuously. An ideal usable length for the prosthesis is considered to be of the order of 15 cm. Each of the leaflets preferably is between 2-½ to 5 inches in width.

Figure 6:
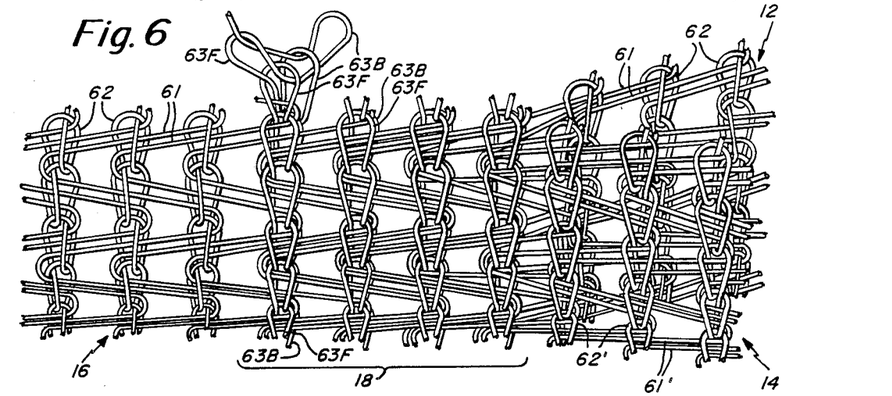
FIG. 6 is an enlarged illustration of the details of the warp knitted fabric used in the preferred embodiment of the invention.

FIG. 6 illustrates, in enlarged detail, a portion of the prosthesis including the core 18 and adjacent panels 12, 14, 16. The full width fabric, which defines the panels 12, 16 of the prosthesis is formed, in a preferred embodiment, from laid in yarns 61 trapped by chain stitches 62. The half width panel, which forms panel 14, similarly is formed from laid in yarns indicated at 61' trapped by chain stitches, indicated at 62'. The region of the core 18 is illustrated, in the preferred embodiment, as being made up of a plurality, preferably four wales of chain stitches 63F, 63B which are stitched from the front needle bed to the back needled bed. In FIG. 6, the stitches designated as 63F represent those made on the front needle bed and the stitches designated at 63B represent those made on the back needle bed. From FIG. 6 it can be seen that yarns 61 are laid in and overlap three wales of chain stitches 62.

The machine is set up preferably on 24 gauge. That stitch construction using monofilament yarn and with a stitch density described below results in a relatively unstretchable fabric which is stable and resists unraveling when trimmed or cut. The fabric is knit to have a quality per rack of between 10 to 15 inches ±½ inch. The fabric preferably has about 13±2 wales per inch and between 17 and 24±2 stitches per inch.

Figure 7:
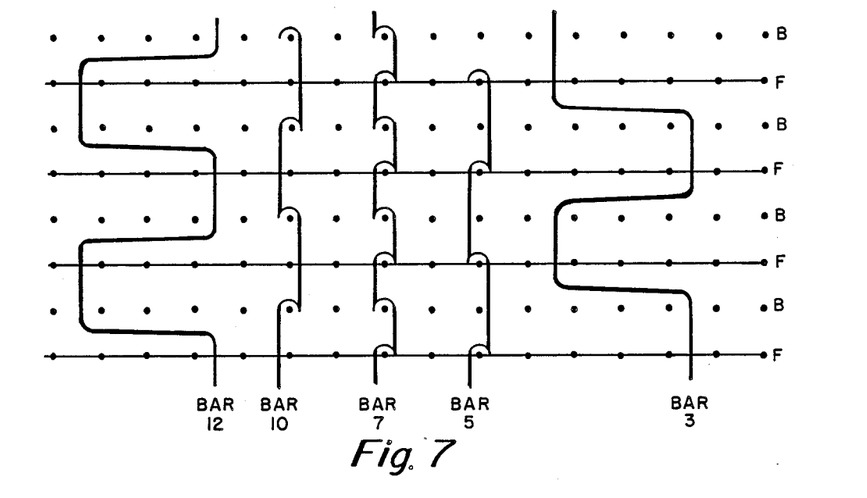
FIG. 7 is a point diagram illustrating the movement of the guide bars in knitting the prosthesis.
Figure 8:
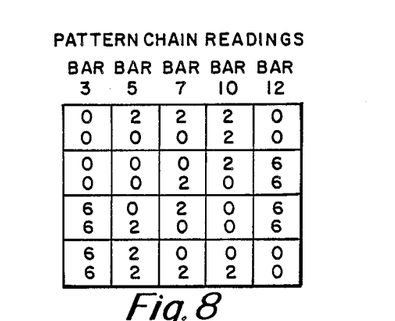
FIG. 8 is a table of pattern chain readings for use in the manufacture of the fabrics.
Figure 9:
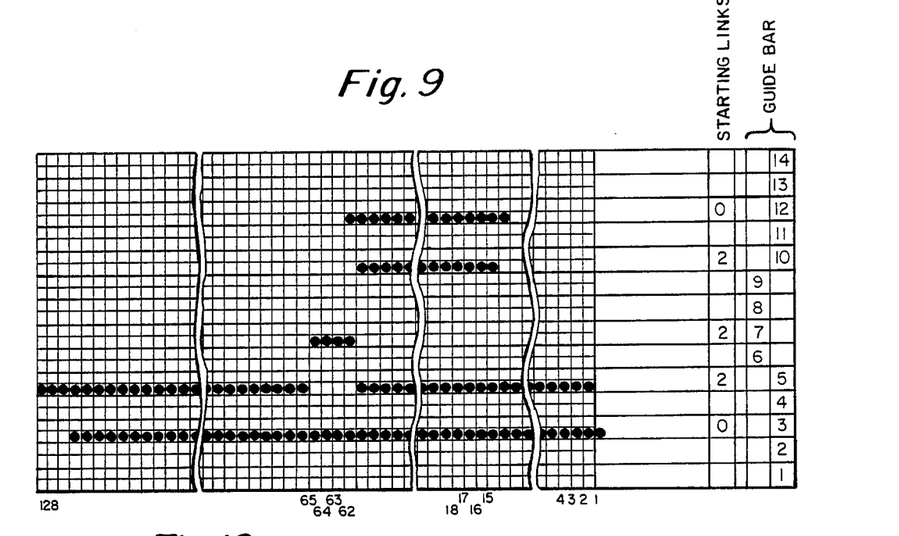
FIG. 9 is a threading diagram for the machine in making the fabric.

FIG. 7 illustrates the stitch pattern, FIG. 8 illustrates the pattern chain readings and FIG. 9 illustrates the threading diagram. From FIGS. 7, 8 and 9 it can be seen that the full width panel is knitted on the front needle bed using two guide bars, one of which is fully threaded and the other of which is fully threaded except for a group of four guides at the center. The half width panel is formed on the back needle bed and also is a two bar fabric with the guide bars fully threaded for the width of the half width panel. Another guide bar (no. 7 in the threading diagram) is threaded along the four guides corresponding to the unthreaded guides in one of the guide bars (no. 5 in the illustration). The guide bar with four threaded guides is controlled to make a chain stitch on each bed, front to back, to stitch the margin of the half width fabric knitted on the back needle bed to the midportion of the full width fabric being knitted on the front needle bed. The resulting product forms a core 18 which is relatively unbulky and a fabric having the desired characteristics described above.

In the illustrative embodiment, the runners per rack for bars no. 3 and no. 12 should be between 48 and 53 inches, for bars no. 5 and no. 10 should be between 48 and 58 inches and for bar no. 7, between 80 and 100 inches.

Figures 10, 11, 12, 13:
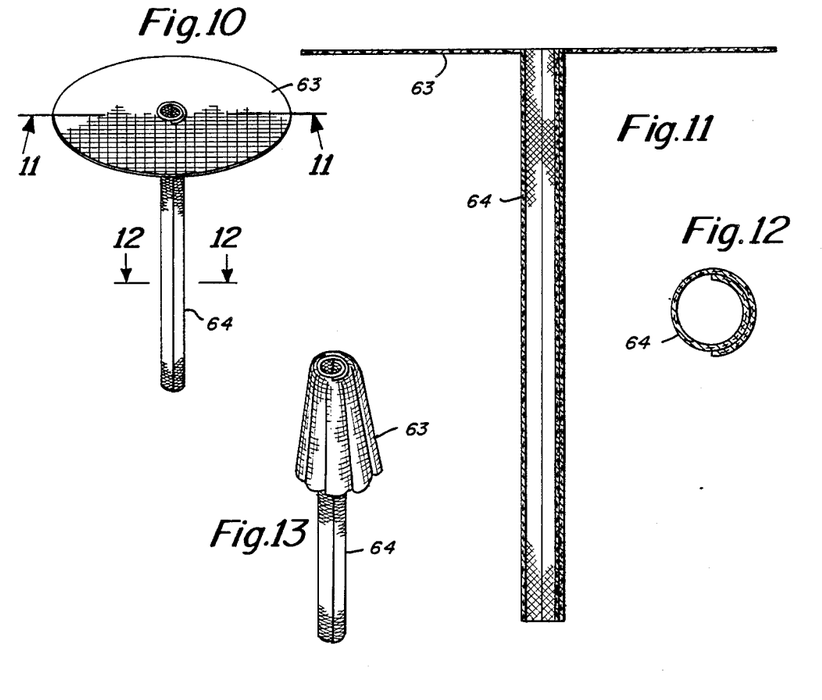
FIG. 10 is an illustration of the prosthetic device used to repair femoral hernias.
FIG. 11 is a cross-sectional illustration of the device showing in FIG. 10 as seen along the line 11—11 of FIG. 10.
FIG. 12 is a cross-sectional illustration of the stem as seen along the line 12—12 of FIG. 10.
FIG. 13 is an illustration of the prosthetic device shown in FIG. 10 with the top panel folded umbrella-like about the stem, to facilitate insertion of the device through the herniated femoral opening.

FIGS. 10, 11 and 12 show a prosthesis used in repair of femoral hernias. The device is somewhat umbrella-shaped including a top panel 63 and a stem 64 which is attached to and extends from the face of the top panel 63. The top panel 63 is formed from a flexible biocompatible material and may be knitted in a mesh from the same polypropylene monofilament and in the same fabric described above in connection with the inguinal prosthesis. The stem 64 may be formed from any biocompatible material and may, for example, be formed from a rolled up portion of a knitted fabric of the same yarn from which the top panel 63 is made. The stem 64 is intended to serve as a handle by which the device may be manipulated into a position in which the top panel 63 overlies the herniated region of the femoral ring, as will be described, so as to prevent further hernia in the region. Once the top panel 63 has been manipulated and sutured in place, the stem 64 is cut away from the panel 63, to leave the panel 63 in place.

Figure 14:
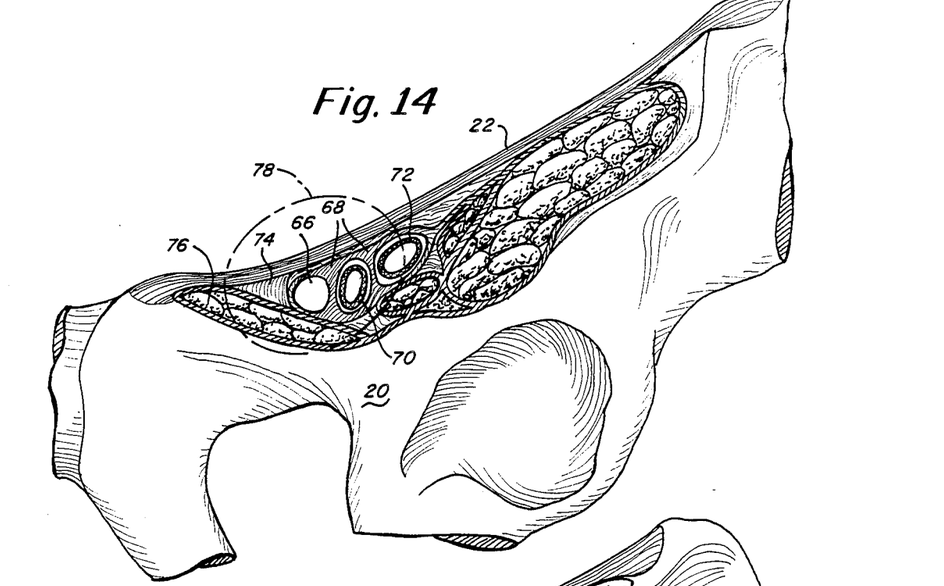
FIG. 14 is an illustration of the anatomy of the region of the femoral ring with the position of the prosthetic device of FIG. 10 shown in phantom.

FIG. 14 is a sectional illustration of the right pelvic region as seen from below illustrating the femoral ring, indicated at 66, through which femoral hernias occur. The femoral ring 66 anatomically resembles a funnel having a wide upper opening and a narrowed lower opening. The somewhat circular ring shown at 66 in FIG. 14 illustrates the wider upper opening. A femoral hernia results when the peritoneum pushes downwardly (toward the viewer in FIG. 14) through the femoral ring 66. The femoral ring 66 is located next to and medially of the femoral sheath 68 which contains the femoral vein 70 and femoral artery 72. The femoral ring is bounded anteriorally and superiorally by the inguinal ligament 22, medially by the lacunar ligament 74 and posteriorally by the pectineal muscle 76 and Cooper's ligament. The circular outline indicated in phantom at 78 in FIG. 13 illustrates generally the outline of the top panel 63 of the prosthesis as it would be positioned over the femoral ring 66 in a flattened and expanded circular configuration.

Figure 15:
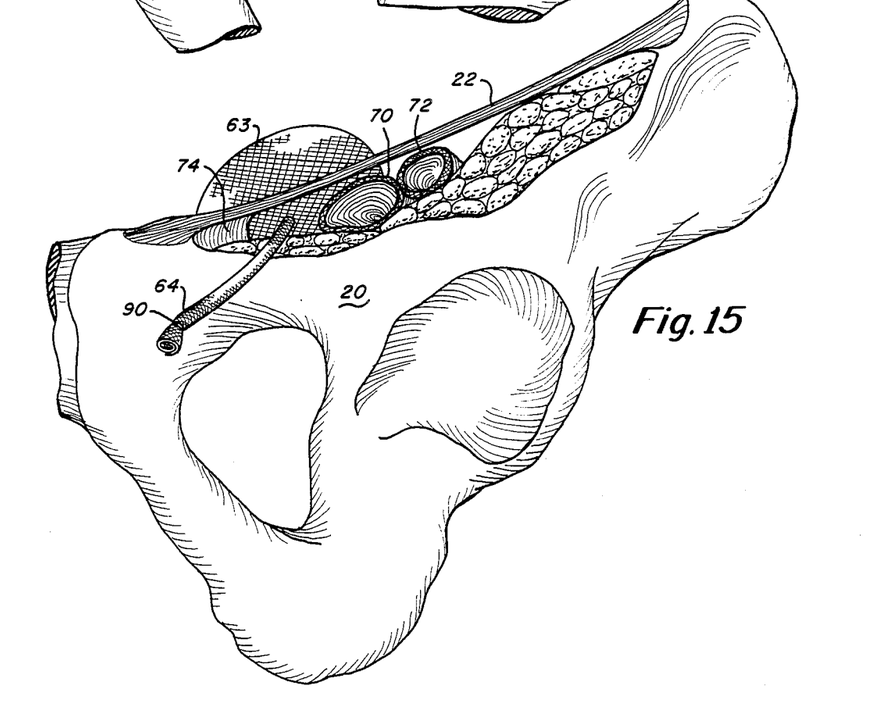
FIG. 15 is a simplified illustration of the placement and attachment of the femoral prosthesis as seen from within the pelvic region and above the region of the femoral ring and inguinal ligament.
Figure 16:
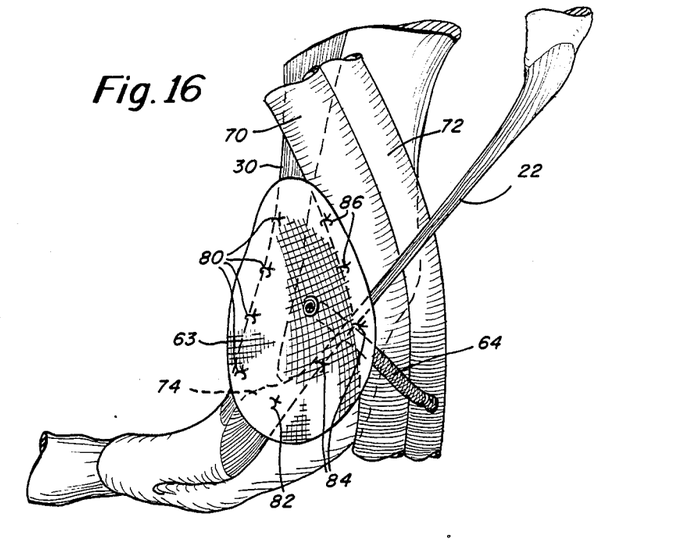
FIG. 16 is an illustration of the placment and attachment of the prosthesis as seen from outside of the pelvis and below the region of the femoral ring and inguinal ligament.

FIGS. 15 and 16 are simplified illustrations of the region of the femoral ring and inguinal ligament, showing the location of placement of the prosthesis. FIG. 15 is an illustration of the placement of the prosthesis as seen from below and outside of the pelvis. FIG. 16 is an illustration as seen from a position within the pelvis above, forwardly and obliquely of the femoral region.

The prosthesis may be placed in a relatively simple surgical procedure requiring only local anesthesia, particularly if the femoral hernia is not too large. Under those conditions, the device is placed from an entry below the femoral ring 66. An incision is made below the level of the femoral ring 66 and parallel to the inguinal ligament. The peritoneal sac which will have pushed through the femoral ring is pushed back upwardly through the femoral ring. The prosthetic device then is gripped by the stem 64, with the top panel 63 being folded down in umbrella-like fashion about the stem 64 as suggested in FIG. 13. In that configuration, the prosthesis is pushed upwardly through the femoral ring until the top panel 63 is above the inguinal ligament. The top panel 63 is permitted to expand and, in that configuration, spans the region of the femoral ring extending from the femoral sheath to the lacunar ligament 74. Although it is difficult to place sutures from beneath, a suture may be placed in the lacunar ligament 74, the inguinal ligament 22 and, posteriorly, to Cooper's ligament. It also is preferred to suture the panel 63 to the femoral sheath if the patient's anatomy lends itself to placing such a suture. The suture to the femoral sheath is not to provide structural support for the top panel 63 but merely to prevent that portion of the panel 63 which lies against the femoral sheath from separating from it. After the top panel 63 is placed, the stem 64 is severed and removed. Thus, the top panel 63 of the prosthesis lies above the femoral ring and effectively prevents any recurrence of a femoral hernia.

In some cases, such as when the femoral hernia is relatively large, additional suturing may be necessary to assure that the device will remain securely in position. In those circumstances, it may be necessary to perform the repair from above, i.e., from the preperitoneal cavity where the top side of the top panel 63 is more accessible. FIG. 16 illustrates somewhat the manner in which the prosthesis would be presented as viewed from the prepectineal space. From that angle, it is possible to suture the panel 63 to Cooper's ligament 30, as indicated at sutures 80, to the lacunar ligament 74 as indicated by the suture 82 and to the inguinal ligament 22 as indicated by the sutures 84. The portion of the panel 63 which lies against the femoral sheath may be attached to the femoral sheath by a suture 86.

As mentioned above, the fabric for the top panel may be the same as the fabric from which the inguinal prosthesis 10 is formed. The stem 64 also may be formed from a knitted mesh of material which is curled into the stem shape and heat set in the curled configuration. Any of a wide variety of well known knitting patterns may be used and the fabric may be a one bar fabric. By way of example, the fabric may be of the kind which is commercially available from C. R. Bard, Inc. of Billerica, Mass. under the designation Marlex mesh. The ends of the stem 64 may be secured by tying a short length of filament 90 about the ends. The stem 64 may be attached by sewing it to the top panel 63. The top panel preferably is cut from a larger sheet of fabric by a heat sealing die cut so that the heat seal may fuse the cut filaments and further secure the stability of the top panel 63.

It should be understood that the foregoing description of the invention is intended merely to be illustrative and that other embodiments and modifications may be apparent to those skilled in the art without departing from its spirit.

Having thus described the invention, what we desire to claim and secure by letters patent is:

1. A prothesis for the repair of an inquinal hernia comprising:
   three panels of flexible porous material joined to each other along a common core and radiating from the core;
   said panels being formed from a knitted fabric of monofilament yarn;
   said fabric being a warp knit fabric formed from laid in yarns trapped by chain stitches and having a stitched density which provides a stable fabric resistant to unraveling when cut and which is relatively unstretchable wale wise as well as coarse wise.

2. A prosthesis as defined in claim 1 further comprising:
   said prosthesis comprising a full width portion and a half width portion, the edge of the half width portion being connected to the midline of the full width portion by chain stitches;
   the knitted juncture of the half width and full width sections defining the core.

3. A prosthesis as defined in claim 2 wherein the core is at least 15 centimeters long and in which each of the three panels have a width of between 2½ to 5 inches.

4. A prosthesis as defined in claim 2 wherein the yarn is of 6 mil polypropylene yarn of the order of 150 denier.

5. A fabric as set forth in claim 1 wherein the laid in yarns are laid into overlap three wales of chain stitches.

6. A method for repair of an inguinal hernia comprising:
   providing a prosthesis having three panels of flexible porous material joined to each other along a common core and radiating from the core.
   anchoring the ends of the coare to the region of the anterior superior iliac spine and the pubic tubical;
   attaching one of the panels to Cooper's ligament;
   attaching a second of the panels to the combined transversalis and internal oblique muscles; and
   attaching the third of the panels to the external oblique aponeuroses.

* * * * *